(12) United States Patent
Engelbart et al.

(10) Patent No.: US 6,940,295 B2
(45) Date of Patent: Sep. 6, 2005

(54) APPARATUS AND METHODS FOR NON-DESTRUCTIVE INSPECTION USING MICROWAVE SENSING

(75) Inventors: Roger W. Engelbart, St. Louis, MO (US); David F. Fortner, Sullivan, MO (US); Nancy L. Wood, Clayton, MO (US)

(73) Assignee: The Boeing Company, Chicago, IL (US)

(*) Notice: Subject to any disclaimer, the term of this patent is extended or adjusted under 35 U.S.C. 154(b) by 0 days.

(21) Appl. No.: 10/459,957

(22) Filed: Jun. 11, 2003

(65) Prior Publication Data

US 2004/0251920 A1 Dec. 16, 2004

(51) Int. Cl.⁷ .............................................. G01R 27/08
(52) U.S. Cl. ...................... 324/700; 324/642; 324/71.2
(58) Field of Search ................................ 324/637–642, 324/534, 633, 634, 700, 71.2, 643

(56) References Cited

U.S. PATENT DOCUMENTS

| | | | |
|---|---|---|---|
| 4,800,165 A | 1/1989 | Oka et al. | 205/777 |
| 4,977,377 A | 12/1990 | Durrett et al. | 324/640 |
| 5,001,434 A | 3/1991 | Marrelli et al. | 324/640 |
| 5,049,816 A * | 9/1991 | Moslehi | 324/767 |
| 5,532,589 A | 7/1996 | Gammell | 324/228 |
| 5,576,627 A | 11/1996 | McEwan | 324/639 |
| 5,648,038 A | 7/1997 | Fathi et al. | 264/406 |
| 5,905,376 A | 5/1999 | Synderman et al. | 324/300 |
| 6,105,695 A * | 8/2000 | Bar-Cohen et al. | 180/8.5 |
| 6,411,105 B1 | 6/2002 | Liu | 324/639 |
| 6,674,292 B2 * | 1/2004 | Bray et al. | 324/637 |

* cited by examiner

*Primary Examiner*—Vincent Q. Nguyen
(74) *Attorney, Agent, or Firm*—Black Lowe & Graham, PLLC

(57) ABSTRACT

Apparatus and methods for materials inspection using microwave sensing are disclosed. In one aspect, a system for detecting corrosion of a workpiece includes a scanning assembly having a support assembly adapted to be coupled to the workpiece, and a first translation device coupled to the support assembly. A microwave sensor is coupled to the first translation device. The first translation device is adapted to translate the microwave sensor along at least a first direction, and the microwave sensor is adapted to transmit incident microwave signals onto the workpiece and to receive reflected microwave signals reflected from the workpiece. In an alternate aspect, a system may further include a second translation device that is adapted to translate the microwave sensor along at least a second direction that is transverse to the first direction.

31 Claims, 3 Drawing Sheets

APPARATUS AND METHODS FOR NON-DESTRUCTIVE INSPECTION USING MICROWAVE SENSING

FIELD OF THE INVENTION

The present disclosure relates to apparatus and methods of non-destructive inspection, and more specifically, to non-destructive inspection of corrosion using microwave sensing.

BACKGROUND OF THE INVENTION

Detection and repair of corrosion is an important issue in the world of aviation. When an aircraft undergoes conventional corrosion inspection and repair procedures, the aircraft may spend up to several months in a depot facility awaiting completion of the inspection, disassembly, repair, replacement, and re-assembly procedures. Typically, a significant portion of this downtime may be attributable to the unavailability of replacement parts or spares. Replacement parts are often ordered from a supplier only when the need becomes known. Because conventional field-level inspections of aircraft are usually limited to visual inspections, the actual extent of corrosion in an aircraft structure may not be determined until more extensive, depot-level inspections are performed. As a result, the need for replacement parts may not be identified when the aircraft is in the field, but rather, may only become known when the aircraft reaches the depot and is disassembled. Therefore, there exists an unmet need for apparatus and methods for conducting field-level inspections of aircraft to provide an early assessment of the extent of corrosion in an aircraft structure and to facilitate the ordering of replacement parts prior to the aircraft's arrival at the depot.

SUMMARY OF THE INVENTION

The present invention is directed to apparatus and methods for materials inspection using microwave sensing. Apparatus and methods in accordance with the present invention may advantageously provide improved detection and characterization of the presence of corrosion during on-site field testing, and may provide more efficient and accurate determinations of corrosion over a two dimensional area of a workpiece, in comparison with alternate methods.

In one embodiment, a system for detecting corrosion of a workpiece includes a scanning assembly having a support assembly adapted to be coupled to the workpiece, and a first translation device coupled to the support assembly. A microwave sensor is coupled to the first translation device. The first translation device is adapted to translate the microwave sensor along at least a first direction, and the microwave sensor is adapted to transmit incident microwave signals onto the workpiece and to receive reflected microwave signals reflected from the workpiece. In an alternate embodiment, a system may further include a second translation device that is adapted to translate the microwave sensor along at least a second direction that is transverse to the first direction.

BRIEF DESCRIPTION OF THE DRAWINGS

The preferred and alternative embodiments of the present invention are described in detail below with reference to the following drawings.

DETAILED DESCRIPTION OF THE INVENTION

The present invention relates to apparatus and methods for materials inspection using microwave sensing. Many specific details of certain embodiments of the invention are set forth in the following description and in FIGS. 1–7 to provide a thorough understanding of such embodiments. One skilled in the art, however, will understand that the present invention may have additional embodiments, or that the present invention may be practiced without several of the details described in the following description.

Figure 1:
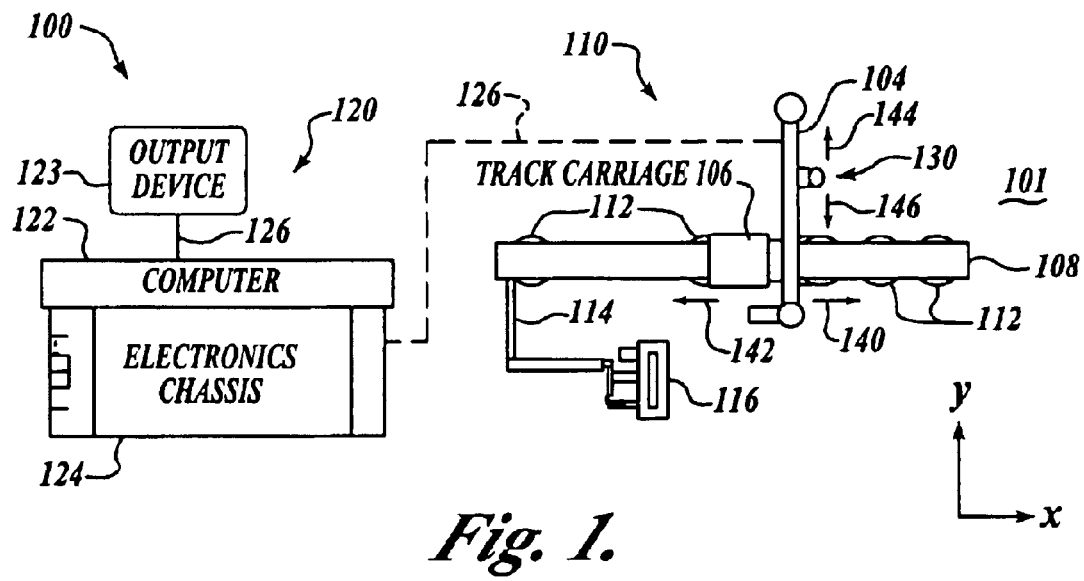
FIG. 1 is a schematic view of a test system for conducting non-destructive inspections using microwave sensing in accordance with an embodiment of the invention.
Figure 2:
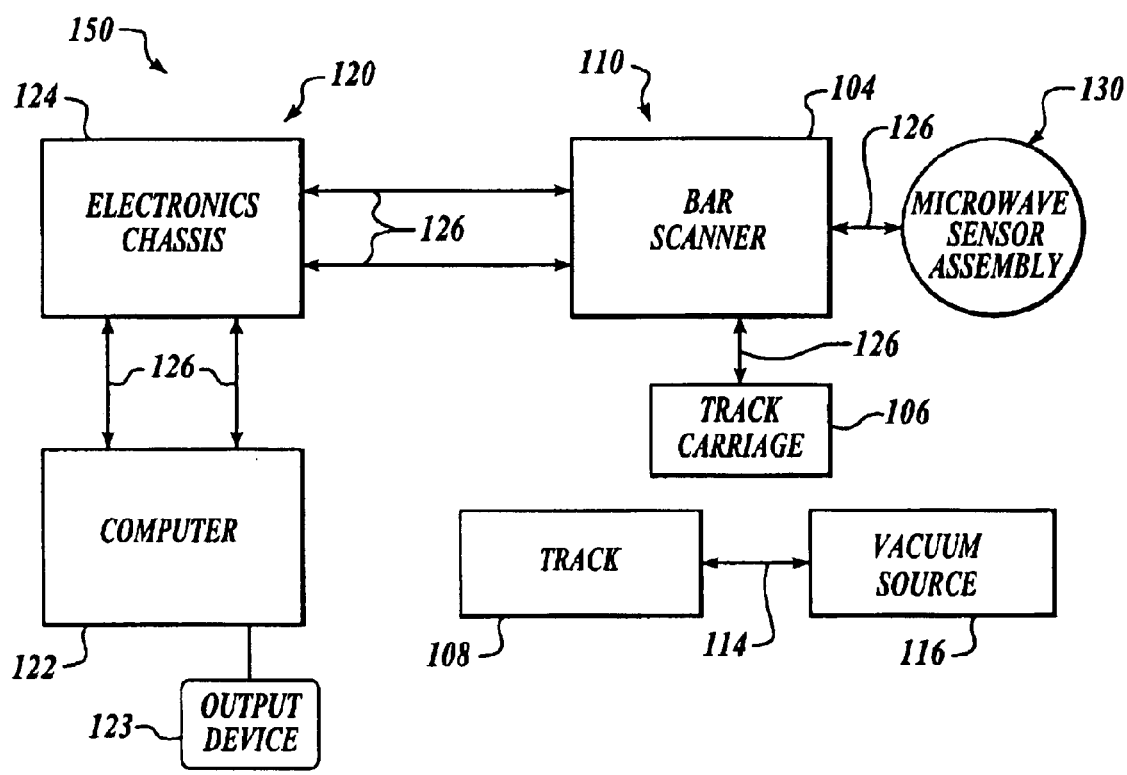
FIG. 2 is a block diagram of the test system of FIG. 1.

FIG. 1 is a schematic view of a test system 100 for conducting non-destructive inspections using microwave sensing in accordance with an embodiment of the present invention. FIG. 2 is a block diagram 150 of the test system 100 of FIG. 1. In this embodiment, the test system 100 includes a scanning assembly 110 that includes a microwave sensor assembly 130 attached to a bar scanner 104 that is, in turn, moveably attached to a track carriage 106. An elongated track 108 supports the track carriage 106 and is attachable to a workpiece 101 by a plurality of vacuum cup assemblies 112. The vacuum cup assemblies 112 are fluidly coupled to one or more vacuum lines 114 leading to a vacuum source 116, such as a vacuum pump or the like.

As further shown in FIGS. 1 and 2, the test system 100 has a control system 120 that includes a computer 122 coupled to an electronics chassis 124 by one or more signal leads 126. The computer 122 may include a CPU and one or more memory devices that house software that may perform data acquisition, analysis, processing, and display functions. An output device 123, such as a display or a printer, is coupled to the computer 122 by a signal lead 126 for outputting test results. The electronics chassis 124 may contain one or more circuit boards that enable the test system 100 to operate in different modes of operation. As best shown in FIG. 2, in this embodiment, additional signal leads 126 are coupled between the control system 120 and the scanning assembly 110 (e.g. between the electronics chassis 124 and the bar scanner 104), and between the bar scanner 104 and the microwave sensor assembly 130 and the track carriage 106. It may be appreciated that the control system 120 may be a conventional control system, including, for example and not by way of limitation, the control system 120 of a conventional test system known as the Mobile Automated Scanner (MAUS) commercially-available from The Boeing Company, of Chicago, Ill.

It may be appreciated that the vacuum cup assemblies 112 are of known construction and may be of the type described, for example, in U.S. Pat. No. 6,467,385 B1 issued to Buttrick et al., or U.S. Pat. No. 6,210,084 B1 issued to Banks et al. The vacuum from the vacuum source 116 may be controllably applied to (and removed from) the vacuum cup assemblies 112 during, for example, mounting, re-positioning, and removal of the track 108 to and from the workpiece 101. In alternate embodiments, the vacuum cup assemblies 112 may be replaced with other types of attachment assemblies, including magnetic attachment assemblies, bolts or other threaded attachment members, or any other suitable attachment assemblies. Furthermore, it may also be appreciated that the track 108 may be flexible to enable the track 108 to bend and twist to follow the surface of a contoured workpiece, or alternately, may be rigid.

Figure 3:
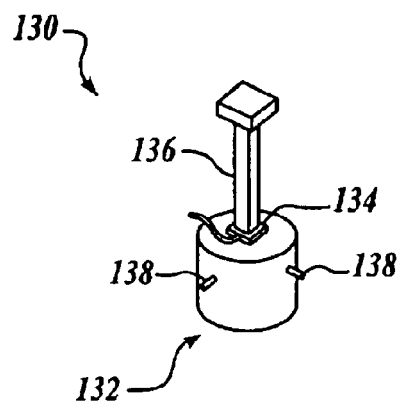
FIG. 3 is an isometric view of a microwave sensor assembly of the test system of FIG. 1 in accordance with an embodiment of the invention.
Figure 4:
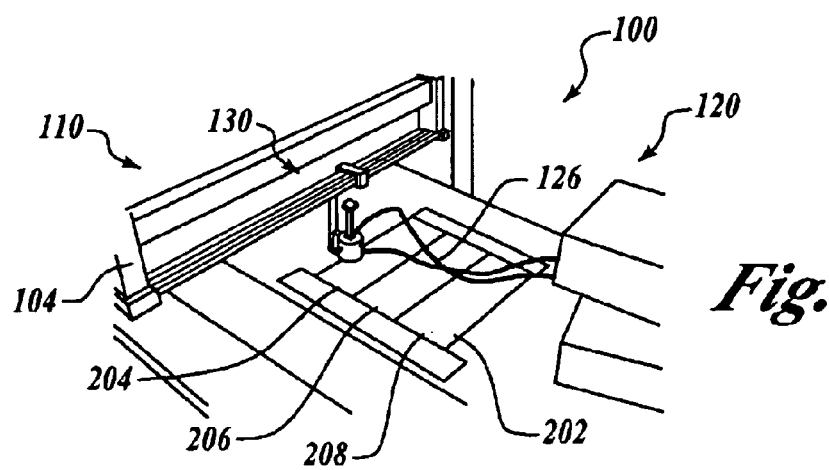
FIG. 4 is an isometric view of the microwave sensor assembly in operation on the bar scanner over a relatively flat workpiece.

FIG. 3 is an enlarged isometric view of the microwave sensor assembly 130 in accordance with an embodiment of the present invention. FIG. 4 is an enlarged isometric view of the microwave sensor assembly 130 mounted to the bar scanner 104 of the test system 100 of FIG. 1. In this embodiment, a microwave sensor (or waveguide) 132 is mounted within a sensor collar 134. A coupling member 136 extends from the sensor collar 134 and attaches to the bar scanner 104. Contacts 138 extend outwardly from the microwave waveguide 132 through the sensor collar 134 to be coupled to one or more signal leads 126 to receive control signals from, and transmit test data to, the control system 120.

It will be appreciated that the microwave sensor 132 is of known construction and its principles of operation are understood. In brief, the microwave sensor 132 transmits microwaves onto the workpiece 102, and reflected microwave signals are sensed by the microwave sensor 132. The reduction in the energy level between the transmitted microwaves and the reflected microwaves provides a measurement of the microwave energy absorbed by the workpiece 102. Post-processing of the energy absorption measurements, which may include accounting for variations in an intensity field of the incident microwaves, provides an estimate of the corrosion levels of the targeted portion of the workpiece 102. The microwave sensor 132 and its related components may of any known type, including, for example, those sensor assemblies disclosed in U.S. Pat. No. 6,411,105 issued to Lui, and in U.S. Pat. No. 5,648,038 issued to Fathi et al., which patents are incorporated herein by reference, or may include any other suitable microwave sensor assemblies. In one embodiment, the microwave sensor assembly 130 employs reflectometers having an open-ended rectangular waveguide 132 that may operate in the Ka band (26.5 to 40 GHz). In alternate embodiments, the waveguide 132 may operate in the V band (50 to 75 GHz), the U band (40 to 60 GHz), and the W band (75 to 110 GHz), or any other suitable range.

FIG. 4 is an isometric view of the microwave sensor assembly 130 mounted on the bar scanner 104 over a relatively flat workpiece 202. In this embodiment, the workpiece 202 includes a first portion 204 having a coating of paint, a second portion 206 having a coating of applique, and a third portion 208 that is bare metal.

In operation, the vacuum cup assemblies 112 are attached to the workpiece 202 such that the microwave sensor assembly 130 is positioned proximate the surface of the workpiece 202. In response to appropriate inputs to the control system 120 by an operator, the control system 120 transmits control signals to the scanning assembly 110 causing the microwave sensor assembly 130 to pass over the surface of the workpiece 202. Preferably, the microwave sensor 132 is positioned in close proximity (near contact) to the workpiece 202. As shown in FIG. 1, the track carriage 106 may translate in first and second directions 140, 142 along the longitudinal axis of the track 108 (e.g. along the x axis), and the bar scanner 104 may translate the microwave sensor assembly 130 in third and fourth directions 144, 146 along the bar scanner 104 (e.g. along the y axis). Thus, the scanning assembly 110 may systematically scan the microwave sensor assembly 130 over a single, linear path, or may scan over a series of sweeps along either the x or y axes to scan a two dimensional area of the workpiece 202.

As the scanning assembly 110 is traversing the microwave sensor assembly 130 over the desired area of the workpiece 202, the waveguide 132 may transmit microwaves toward the workpiece 202 and receive reflected microwaves from the workpiece 202, and transmit corresponding signals to the control system 120 (FIG. 1). Alternately, the positioning and sensing operations may be conducted sequentially (e.g. in alternating steps) rather than simultaneously. The control system 120 (e.g. the computer 122) may then receive signals from the microwave sensor assembly 130 and may process the signals to estimate a characteristic of the workpiece 102, such as the presence and severity of corrosion of the workpiece 202. The results of the computations may be transmitted to the display 123 for analysis by an operator. It will be appreciated that the incident and reflected microwaves may penetrate the paint and the applique on the first and second portions 204, 206 of the workpiece 202, and may thereby provide indications and estimates of corrosion that are not detectable during an ordinary visual inspection.

Figure 5:
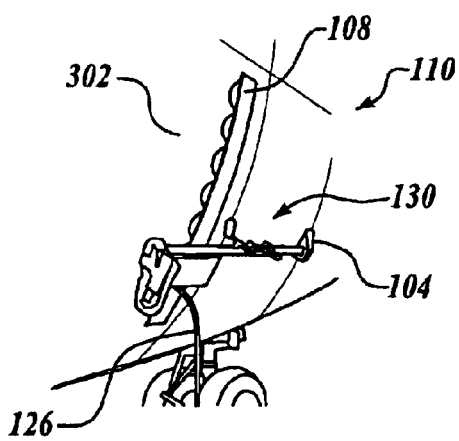
FIG. 5 is an isometric view of the microwave sensor assembly in operation on the bar scanner over a contoured workpiece.

FIG. 5 is an isometric view of the microwave sensor assembly 130 in operation on the bar scanner 104 over a contoured workpiece 302. In this case, the contoured workpiece 302 is an aircraft fuselage. The test device 110 may be operated in the manner described above to efficiently, accurately, and systematically scan the contoured workpiece 302 to provide an assessment of the amount of corrosion present in the aircraft fuselage.

Figure 6:
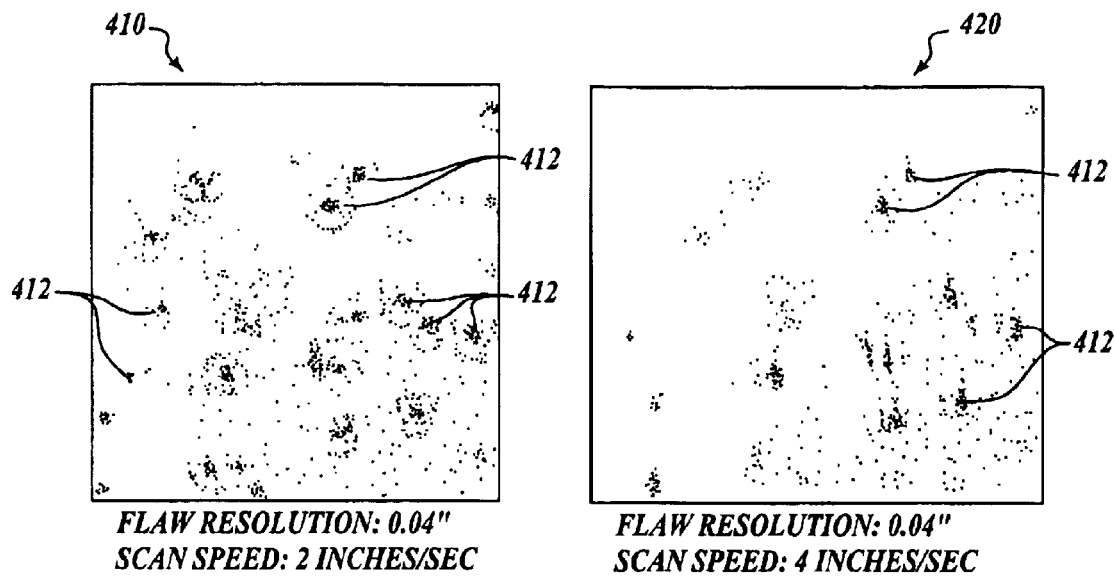
FIG. 6 is an elevational view of a first and second sets of test data obtained using the test system of FIG. 4.

FIG. 6 is an elevational view of a first and second sets of test data 410, 420 obtained using the test system of FIG. 4. The first set of test data 410 was acquired by scanning the bar scanner 104 along the track 108 at a scan speed of 2 inches/sec with the microwave sensor 132 operating at 35 GHz, while the second set of test data 420 was obtained by scanning the bar scanner 104 at a scan speed of 4 inches/sec (with the microwave sensor 132 operating at 35 GHz). In both sets of test data 410, 420, corrosion pits 412 within the surface of the workpiece 101 are visible. The first set of test data 410 (scan speed of 2 inches/sec) provides a better characterization of locations and number of pits 412 than the second set of test data 420 (scan speed of 4 inches/sec). Generally, both of the first and second sets of test data 410, 420 demonstrate the utility of the test system 100 to provide uniform, high-quality characterization of the corrosion characteristics across a two dimensional area of the workpiece 101.

Embodiments of apparatus and methods in accordance with the present invention may provide several advantages over alternate test devices and methods. For example, the test device 100 provides a relatively mobile system for conducting field inspections for the presence of corrosion. The system provides a capability to obtain an early characterization of the presence and level of corrosion in an aircraft structure, and may allow replacement parts to be ordered prior to the arrival of the aircraft at an inspection and repair depot. Thus, embodiments of the present invention may advantageously reduce the amount of time an aircraft or other structure is out of service at the inspection and repair depot.

Furthermore, embodiments of the present invention provide an improved characterization of the corrosion of a workpiece in an accurate and efficient manner. Because the microwave sensor assembly 130 may be mounted on an automated scanning system (e.g. the bar scanner 104, the track 108, and the track carriage 106), the microwave sensor assembly 130 may be uniformly and systematically traversed over a two dimensional area of the workpiece to enable accurate characterization of the corrosion levels of the workpiece. Because the track 108 may be coupled to the workpiece (e.g. using the vacuum cup assemblies 112), the amount of labor associated with the inspection of a workpiece may be reduced and the efficiency of the operation improved. Also, because the track 108 may be flexible, the automated scanning capability afforded by the track 108 may be utilized on a flat workpiece or on a contoured workpiece, such as an aircraft fuselage. Embodiments of the present invention may therefore provide improved characterization of a workpiece more quickly and efficiently, and at a reduced cost, in comparison with alternate test apparatus and methods.

Finally, embodiments of the present invention may provide advantages over alternate test devices when the workpiece is painted or otherwise coated with a layer that impedes visual inspection. Because the microwaves may penetrate non-metallic coatings, the status of corrosion beneath layers of paint and the like may be obtained. Microwaves provide a suitable degree of sensitivity to changes in material properties that enables a suitably accurate characterization of the underlying material without the need to remove the surface coating or otherwise perform destructive measures on the workpiece. Furthermore, because the microwave sensor may operate from a single side of the workpiece, there is no need for to place receivers on the opposite side of the workpiece (e.g. inside an aircraft) in order to characterize the material properties of the workpiece. Overall, embodiments of the present invention may provide a relatively low power, operator friendly, real time and relatively mobile apparatus and methods to perform the desired non-destructive testing.

Figure 7:
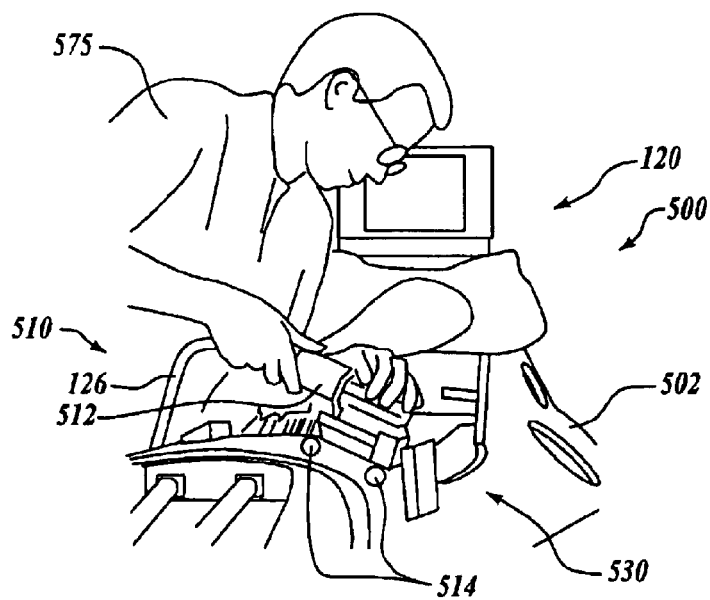
FIG. 7 is an isometric view of a test system for conducting non-destructive inspections using microwave sensing in accordance with an alternate embodiment of the invention.

FIG. 7 is an isometric view of a test system 500 for conducting non-destructive inspections using microwave sensing in accordance with an alternate embodiment of the invention. In this embodiment, the track 108, vacuum pump 116, track carriage 106, and bar scanner 104 have been eliminated. The microwave sensor assembly 530 is mounted on a scan head 510 and is operatively coupled directly to the control system 120 (e.g. by a signal lead 126). The scan head 510 may be coupled to the workpiece 502 by simply pressing or engaging the scan head 510 against the workpiece 502. The scan head 510 may hold one or more microwave sensors 132 in proximity to, or in contact with, the surface of the workpiece 502. A motor 512 in the scan head 510 moves the microwave sensor(s) 132 laterally (side to side) across the workpiece 502 to automatically collect a line of data. As the scan head 510 moves the microwave sensor(s) 132, the control system 120 collects a strip of inspection data that is the width of the scanner stroke multiplied by the number of sensors attached to the scan head 510. The stroke of the scan head 510 may be variable or fixed.

In the embodiment shown in FIG. 7, the scan head 510 includes wheels 514 (two visible) that rollably engage with the workpiece 502. The scan head 510 may be configured to activate with the start of rotation of the wheels 514 (e.g. by encoders that detect wheel rotation) such that the motor 512 starts when the scanner is active and the wheels 514 move forward or backward by a small amount, and stops when the forward or backward motion is stopped. As shown in FIG. 7, the scan head 510 may be moved over the workpiece 101 manually by an operator 575. Alternately, the scan head 510 may be coupled to the track carriage 106 shown in FIG. 1 (with the bar scanner 104 removed), and may be moved in the forward and backward directions along the track 108 (e.g. first and second directions 140, 142 shown in FIG. 1) by the track carriage 106.

The test device 500 may provide the above-noted advantages of non-destructive inspection using microwaves may be achieved in a test device 200 having a relatively smaller scan head 510. Because the track 108, the vacuum pump 116, the track carriage 106, and the bar scanner 104 have been eliminated, the test device 500 may be easier to setup and takedown than alternate test device embodiments. Furthermore, the test device 500 having a relatively smaller scan head 510 may provide advantages when attempting overhead inspections, or in applications where access to the inspection area is limited.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

What is claimed is:

1. A system for detecting corrosion of a workpiece, comprising:
    a scanning assembly including:
        a support assembly adapted to be coupled to the workpiece;
        a first translation device coupled to the support assembly;
    a microwave sensor coupled to the first translation device, wherein the first translation device is adapted to translate the microwave sensor along at least a first direction, and wherein the microwave sensor is adapted to transmit incident microwave signals on the workpiece and to receive reflected microwave signals reflected from the workpiece, and
    a second translation device operatively coupled to at least one of the support assembly, the first translation device, and the microwave sensor, the second translation device being adapted to translate the microwave sensor along at least a second direction that is transverse to the first direction.

2. The system of claim 1, wherein the support assembly includes a track assembly adapted to be coupled to the workpiece, and wherein the first translation device includes a carriage assembly moveably coupled to the track assembly, and wherein the second translation device includes a bar scanner coupled to the carriage assembly.

3. The system of claim 1, wherein the first translation device includes a bar scanner adapted to translate the microwave sensor therealong.

4. The system of claim 1, wherein the first translation device includes a scan head having a motor adapted to translate the microwave sensor.

5. The system of claim 1, further including a control system operatively coupled to the scanning assembly, the control system having a processor and a memory device operatively coupled to the processor.

6. The system of claim 1, further including a control system operatively coupled to the scanning assembly, wherein the control system includes:

a computer having a processor and a memory device operatively coupled to the processor; and an electronics chassis operatively coupled to the computer, the electronics chassis including at least one electronics card.

7. The system of claim 1, wherein the microwave sensor is adapted to operate within at least one of a Ka band, a V band, a U band, and a W band.

8. A system for detecting corrosion of a workpiece, comprising:

a scanning assembly including:
  a support assembly adapted to be coupled to the workpiece;
  a first translation device coupled to the support assembly; and
a microwave sensor coupled to the first translation device, wherein the first translation device is adapted to translate the microwave sensor along at least a first direction, and wherein the microwave sensor is adapted to transmit incident microwave signals onto the workpiece and to receive reflected microwave signals reflected from the workpiece,
wherein the support assembly includes a track assembly adapted to be coupled to the workpiece, and wherein the first translation device includes a carriage assembly moveably coupled to the track assembly.

9. A system for detecting corrosion of a workpiece, comprising:

a scanning assembly including:
  a support assembly adapted to be coupled to the workpiece;
  a first translation device coupled to the support assembly, wherein the first translation device includes a scan head having a motor adapted to translate the microwave sensor, and a wheel that rollably engages the workpiece, the scan head being adapted to activate the motor when the wheel is rolled on the workpiece; and
a microwave sensor coupled to the first translation device, wherein the first translation device is adapted to translate the microwave sensor along at least a first direction, and wherein the microwave sensor is adapted to transmit incident microwave signals onto the workpiece and to receive reflected microwave signals reflected from the workpiece.

10. A system for detecting corrosion of a workpiece, comprising:

a scanning assembly including:
  a support assembly adapted to be coupled to the workpiece, wherein the support assembly includes at least one vacuum cup assembly adapted to be removeably coupled to the workpiece;
  a first translation device coupled to the support assembly; and
a microwave sensor coupled to the first translation device, wherein the first translation device is adapted to translate the microwave sensor along at least a first direction, and wherein the microwave sensor is adapted to transmit incident microwave signals on the workpiece and to receive reflected microwave signals reflected from the workpiece.

11. The system of claim 10, wherein the support assembly further includes a vacuum source operatively coupled to the at least one vacuum cup assembly.

12. A system for conducting non-destructive inspections of a workpiece, comprising:

a control system; and
a data acquisition assembly operatively coupled to the control system, the data acquisition assembly including:
  a scanning assembly adapted to translate the microwave sensor along at least a first direction; and
  a microwave sensor assembly coupled to the scanning assembly and adapted to be positioned proximate the workpiece, the microwave sensor assembly being a further adapted to transmit incident microwave signals onto the workpiece and to receive reflected microwave signals reflected from the workpiece, and to transmit a test signal corresponding to the reflected microwave signals to the control system, wherein the scanning assembly includes:
  a track assembly adapted to be coupled to the workpiece; and
  a carriage assembly moveably coupled to the track assembly and to the microwave sensor assembly, the carriage assembly being adapted to translate along the track assembly in response to a first control signal from the control system.

13. The system of claim 12, wherein the scanning assembly further includes
  a bar scanner coupled to the carriage assembly and to microwave sensor assembly, the bar scanner extending transversely to the track assembly and being adapted to translate the microwave sensor assembly along bar scanner in response to a second control signal from the control system.

14. The system of claim 12, wherein the scanning assembly includes a scan head having a motor adapted to translate the microwave sensor.

15. The system of claim 14, wherein the scan head includes a wheel that rollably engages the workpiece, the scan head being adapted to activate the motor when the wheel is rolled on the workpiece.

16. The system of claim 12, wherein the scanning assembly includes a support assembly coupled to the microwave sensor assembly, the support assembly including at least one vacuum cup assembly adapted to be removeably coupled to the workpiece.

17. The system of claim 16, wherein the scanning assembly further includes a vacuum source operatively coupled to the at least one vacuum cup assembly.

18. The system of claim 12, wherein the control system includes a processor and a memory device operatively coupled to the processor.

19. The system of claim 12, wherein the control system includes:
  a computer having a processor and a memory device operatively coupled to the processor; and
  an electronics chassis operatively coupled to the computer, the electronics chassis including at least one electronics card.

20. The system of claim 19, wherein the control system further includes a display device operatively coupled to at least one of the computer and the electronics chassis.

21. The system of claim 12, wherein the microwave sensor assembly includes a microwave sensor adapted to operate within at least one of a Ka band, a V band, a U band, and a W band.

22. A system for conducting non-destructive inspections of a workpiece, comprising:

a control system; and
a data acquisition assembly operatively coupled to the control system, the data acquisition assembly including:

a scanning assembly adapted to translate the microwave sensor along at least a first direction; and a microwave sensor assembly coupled to the scanning assembly and adapted to be positioned proximate the workpiece, the microwave sensor assembly being further adapted to transmit incident microwave signals onto the workpiece and to receive reflected microwave signals reflected from the workpiece, and to transmit a test signal corresponding to the reflected microwave signals to the control system, wherein the scanning assembly includes:

a support assembly adapted to be coupled to the workpiece; and a bar scanner coupled to the support assembly and to microwave sensor assembly, the bar scanner being adapted to translate the microwave sensor assembly along bar scanner in response to a second control signal from the control system.

23. A method for detecting corrosion of a workpiece, comprising:

providing a microwave sensor coupled to a first translation device of a scanning assembly adapted to translate the microwave sensor, including providing the microwave sensor coupled to a carriage assembly mounted on a track assembly;

coupling the scanning assembly to the workpiece, the microwave sensor being operatively positioned proximate the workpiece;

transmitting microwave energy onto the workpiece;

traversing the microwave sensor over the workpiece using the scanning assembly, including, traversing the microwave sensor along the track assembly using the carriage assembly; and receiving reflected microwave energy reflected from the workpiece.

24. The method of claim 23, wherein transmitting microwave energy onto the workpiece includes transmitting microwave energy onto the workpiece, the microwave energy being within at least one of a Ka band, a V band, a U band, and a W band.

25. The method of claim 23, further including determining a corrosion characteristic based on the reflected microwave energy.

26. A method for detecting corrosion of a workpiece, comprising:

providing a microwave sensor coupled to a first translation device of a scanning assembly adapted to translate the microwave sensor, including providing the microwave sensor coupled to a bar scanner;

coupling the scanning assembly to the workpiece, the microwave sensor being operatively positioned proximate the workpiece;

transmitting microwave energy onto the workpiece;

traversing the microwave sensor over the workpiece using the scanning assembly, including, traversing the microwave sensor along the bar scanner; and receiving reflected microwave energy reflected from the workpiece.

27. A method for detecting corrosion of a workpiece, comprising:

providing a microwave sensor coupled to a first translation device of a scanning assembly adapted to translate the microwave sensor, including providing the microwave sensor coupled to a scan head;

coupling the scanning assembly to the workpiece, the microwave sensor being operatively positioned proximate the workpiece;

transmitting microwave energy onto the workpiece;

traversing the microwave sensor over the workpiece using the scanning assembly, including, traversing the microwave sensor laterally across the scan head; and receiving reflected microwave energy reflected from the workpiece.

28. The method of claim 27, wherein the scan head is adapted to rollably engage with the workpiece, and traversing the microwave sensor over the workpiece includes activating the traversing of the microwave sensor by rolling the scan head on the workpiece.

29. A method for detecting corrosion of a workpiece, comprising:

providing a microwave sensor coupled to a first translation device of a scanning assembly adapted to translate the microwave sensor;

coupling the scanning assembly to the workpiece, the microwave sensor being operatively positioned proximate the workpiece;

transmitting microwave energy onto the workpiece;

traversing the microwave sensor over the workpiece using the scanning assembly; and receiving reflected microwave energy reflected from the workpiece wherein providing a microwave sensor coupled to a first translation device includes, providing a microwave sensor coupled to first and second translation devices, and wherein traversing the microwave sensor over the workpiece includes traversing the microwave sensor along a first direction using the first translation device, and traversing microwave sensor along a second direction using the second translation device, the first and second directions being transverse.

30. The method of claim 29, wherein the first translation device includes a carriage assembly mounted on a track assembly, and wherein the second translation device includes a bar scanner mounted on the carriage assembly.

31. A method for detecting corrosion of a workpiece, comprising:

providing a microwave sensor coupled to a first translation device of a scanning assembly adapted to translate the microwave sensor;

coupling the scanning assembly to the workpiece, the microwave sensor being operatively positioned proximate the workpiece, including applying a vacuum to secure the scanning assembly to the workpiece;

transmitting microwave energy onto the workpiece;

traversing the microwave sensor over the workpiece using the scanning assembly; and receiving reflected microwave energy reflected from the workpiece.

* * * * *